US008987469B2

(12) United States Patent
Frey et al.

(10) Patent No.: US 8,987,469 B2
(45) Date of Patent: Mar. 24, 2015

(54) PROCESS FOR THE PREPARATION OF BENDAMUSTINE

(71) Applicant: Heyl Chemisch-pharmazeutische Fabrik GmbH & Co. KG, Berlin (DE)

(72) Inventors: Michael Frey, Weimar (DE); Dirk-Detlef Walther, Apolda (DE)

(73) Assignee: Heyl Chemisch-pharmazeutische Fabrik GmbH & Co. KG, Berlin (DE)

( * ) Notice: Subject to any disclaimer, the term of this patent is extended or adjusted under 35 U.S.C. 154(b) by 0 days.

(21) Appl. No.: 13/948,182

(22) Filed: Jul. 23, 2013

(65) Prior Publication Data
US 2014/0031560 A1  Jan. 30, 2014

(30) Foreign Application Priority Data

Jul. 24, 2012 (DE) .................... 10 2012 106 736
Jul. 24, 2012 (EP) ................................ 12177730
Apr. 10, 2013 (EP) ................................ 13163191

(51) Int. Cl.
*C07D 235/16* (2006.01)
*C07D 235/12* (2006.01)

(52) U.S. Cl.
CPC ............ *C07D 235/12* (2013.01); *C07D 235/16* (2013.01)
USPC .................................................. 548/310.1

(58) Field of Classification Search
USPC ............................................... 548/310.1
See application file for complete search history.

(56) References Cited

FOREIGN PATENT DOCUMENTS

| CN | 101836962 A | 3/2009 |
|---|---|---|
| CN | 101584668 A | 6/2009 |
| CN | 101606934 A | 7/2009 |
| CN | 101691359 A | 4/2010 |
| CN | 101912369 A | 7/2010 |
| CN | 101966158 A | 9/2010 |
| CN | 101962367 A | 10/2010 |
| CN | 101948436 A | 1/2011 |
| CN | 101948437 A | 1/2011 |
| CN | 102351799 A | 10/2011 |
| CN | 102558069 A | 7/2012 |
| DE | 34727 | 12/1964 |
| DE | 34727 A1 | 12/1964 |
| DE | 159877 A1 | 4/1983 |
| DE | 102010055499 A1 | 6/2011 |
| EP | 1955693 A1 | 8/2008 |
| EP | 1955710 A1 | 8/2008 |
| EP | 1955711 A1 | 8/2008 |
| WO | WO 2008095586 A2 | 8/2008 |
| WO | WO 2008095587 A1 | 8/2008 |
| WO | WO 2008095588 A1 | 8/2008 |
| WO | WO 2009070546 A1 | 6/2009 |
| WO | WO2010/042568 A1 | 4/2010 |
| WO | WO 2010144675 A1 | 12/2010 |
| WO | WO2011/079193 A2 | 6/2011 |
| WO | WO2012/007966 A2 | 1/2012 |
| WO | WO 2012024367 A2 | 2/2012 |
| WO | WO 2012059935 A9 | 5/2012 |
| WO | WO 2012063085 A2 | 5/2012 |
| WO | WO 2012103226 A2 | 8/2012 |
| WO | WO 2012106117 A1 | 8/2012 |
| WO | WO 2012115885 A1 | 8/2012 |
| WO | WO 2012176214 A2 | 8/2012 |
| WO | WO 2013046223 A1 | 4/2013 |

OTHER PUBLICATIONS

Cai et al. "Optimization of synthetic process of Bendamustin" *Journal Yaoxue Shijian Zazhi* (2011), 29(6), 453-454 Abstract Only.
Chen et al. "Discovery of a Novel, Efficient, and Scalable Route to Bendamustine Hydrochloride: The API in Treanda" *Organic Process Research Development* (2011), 15(5), 1063-1072 Abstract Only.
Gao et al. "Synthesis of Bendamustine" *Chinese Journal of New Drugs (Zhongguo Xinyao Zazhi)* (2007), 16(23), 1960-1961, 1970 Abstract Only.
Ozegowski and Krebs, "ω-(Bis-(β-chloräthyl)-amino-benzimidazolyl-(2)]-propion-bzw.-buttersäuren als potentielle Cytostatika," *Journal für praktische Chemie*, 20:178-186, 1963.
Werner et al. "Synthesis of a potential metabolite of the anticancer drug bendamustine (Cytostasen)" *Journal Pharmazie* (1991), 46(2), 113-14 Abstract Only.

(Continued)

*Primary Examiner* — Laura L. Stockton
(74) *Attorney, Agent, or Firm* — JMB Davis Ben-David (57) ABSTRACT

The present invention relates to a method for preparation of alkyl 4-[5-[bis(2 -hydroxyethyl)amino]-1-methyl-1H-benzimidazol-2-yl]butanoate (7) from 2-fluoro-5-nitroaniline, comprising the steps of: (a) conversion of 2-fluoro-5-nitroaniline to 5-(2-fluoro-5-nitroanilino)-5 -oxopentanoic acid (1) using glutaric anhydride, conversion of compound (1) to methylammonium 5-[2-(methylamino)-5-nitroanilino]-5-oxopentanoate (2) using methylamine; conversion of compound (2) to 5[2-(methylamino)-5-nitroanilino]-5-oxopentanoic acid (3) and condensation of compound (3) to 4-(1-methyl-5-nitro-1H-benzimidazol-2-yl)butanoic acid (4); (b) esterification of the product (4) of step a) to alkyl 4-(1-methyl-5-nitro 1H-benzimidazol-2-yl)butanoate (5); (c) reduction of the product of step b) to alkyl 4-(5-amino-l-methyl-1H-benzimidazol-2-yl)butanoate (6), and (d) conversion of the product of step c) to alkyl 4-[5-[bis(2-hydroxyethyl)amino]-1-methyl -1H-benzimidazol-2-yl]butanoate (7).

15 Claims, 5 Drawing Sheets

(56) References Cited

OTHER PUBLICATIONS

Werner et al. "Synthesis of a homolog of bendamustin (Cytostasan) for use as a standard in high performance liquid chromatography" *Journal Pharmazie* (1990), 45(1), 61.

Yan-feng Dai et al. "Synthesis of bendamustine hydrochloride" *Chemical Reagents* (*Huaxue Shiji*) (2010), 32(8), 753-755 Abstract Only.

Fritsch et al., "Quantitative stereological studies on the mechanism of immunosuppressive effect of nitrogen mustards of benzimidazole derivatives: the role of polymorphonuclear leukocytes and mononuclear phagocytes", *Journal Experimentelle Pathologie* (1967-1980) (1979), 17(7-8), 446-60 Abstract Only.

Process for Preparing 4-[5-[Bis(2-Chloroethyl)Amino]-1-Methylbenzimidazol-2-YL] Butanoic Acid Intermediate Available online at ip.com IP.com No. IPCOM000185126D Electronic Publication Date: Jul. 13, 2009.

"Process for Preparing 4-[5-[Bis(2-Chloroethyl)Amino]-1-Methylbenzimidazol-2-YL] Butanoic Acid Intermediate" Available online at ip.com IP.com No. IPCOM000185126D Electronic Publication Date: Jul. 13, 2009.

PROCESS FOR THE PREPARATION OF BENDAMUSTINE

CROSS REFERENCE TO RELATED APPLICATIONS

This application claims priority to European patent applications No. EP13163191.3, filed Apr. 10, 2013 and EP12177730.4, filed Jul. 24, 2012; and Germany patent application No. DE102012106736.8, filed Jul. 24, 2012. The contents of these applications are incorporated by reference in their entirety.

BACKGROUND

The present invention relates to a process for the preparation of 4-[5-[bis(2-chloroethyl)amino]-1-methyl-1H-benzimidazol-2-yl]butanoic acid (9, Bendamustine) starting from 2-fluoro-5-nitroaniline and proceeding through the intermediates 5-(2-fluoro-5-nitroanilino)-5-oxopentanoic acid (1), 5-[2-(methylamino)-5-nitroanilino]-5-oxopentanoic acid (3) and 4-[5-[bis(2-hydroxyethyl)amino]-1-methyl-1H-benzimidazol-2-yl]butanoate (7) and a process for the preparation of said intermediate 4-[5-[bis(2-hydroxyethyl)amino]-1-methyl-1H-benzimidazol-2-yl]butanoate (7).

Bendamustine belongs to the alkylating agent class of compounds, in particular to the nitrogen mustard derivatives. As an antitumoral chemotherapeutic agent it is used both for the treatment of hematological tumours such as non-Hodgkin's and Hodgkin's lymphoma, mantle cell lymphoma, chronic lymphocytic leukaemia or multiple melanoma, as well as for the treatment of solid tumours such as breast cancer or small cell lung cancer.

The compound was first described in 1963 by Ozegowski and Krebs (see Ozegowski W, Krebs D. Aminosäureantagonisten. III. ω-[Bis-(β-chloräthyl)-amino-benzimidazolyl-(2)]-propion-bzw.-buttersäuren als potentielle Cytostatika. J. Prakt. Chem., 1963 Jun.; 20 (3-4): 178-186, and references cited therein) and was marketed under the name Cytostasan. In 1993, the compound was approved in Germany under the name Ribomustin. In 2008 the compound was approved by the FDA for the treatment of B-cell non-Hodgkin's lymphoma and chronic lymphocytic leukaemia under the trade name Treanda.

Numerous synthetic routes for the preparation of Bendamustine are known in the prior art.

Ozegowski et al. (1963) describe the synthesis of Bendamustine starting from N1-methyl-4-nitrobenzene-1,2-diamine.

The synthesis of Bendamustine starting from 1-methylamino-2,4-dinitrobenzene or 2,4-dinitroaniline is described in WO2010042568. The alkylation of the 1-methyl-5-aminobenzimidazole derivative to Bendamustine alkyl ester takes place directly to the crude Bendamustine alkylester with chloroacetic acid, chloroacetic acid ester or chloroacetaldehyde and subsequent reduction with borane-THF complex (reductive amination).

DD34727 describes a process for the preparation of N1-substituted derivatives of Bendamustine, wherein the alkylation of the 1-methyl-5-aminobenzimidazole derivative is performed with ethylene oxide.

WO2011079193 describes the alkylation of a 1-methyl-5-amino-benzimidazole derivative to the precursor of Bendamustine (bishydroxy compound) using 2-Haloethanols in the presence of an organic base.

An analogous alkylation of a 1-methyl-5-amino-benzimidazole derivative in the presence of inorganic bases such as sodium or potassium carbonate is described in WO2012007966 and IPCOM000185126D.

The known processes for the production of Bendamustine exhibit a number of disadvantages, such as the formation of by-products or low yields. In particular, the yield of the favoured procedure in WO2011079193 (using Hünig's base) is not greater than 44.5% and gives a purity of 97.6%.

Some reaction steps are not implementable in large scale or industrial processes. Often, ethylene oxide, a toxic and explosive gas, is used during the synthesis. The use of this gas is unfavourable for reasons of occupational safety.

DESCRIPTION OF THE DISCLOSURE

The objective of the present invention is to provide means and methods that enable an economical preparation of Bendamustine whilst avoiding the disadvantages of the methods known in the art. This objective is attained by the subject matter of the independent claims.

Figure 1:
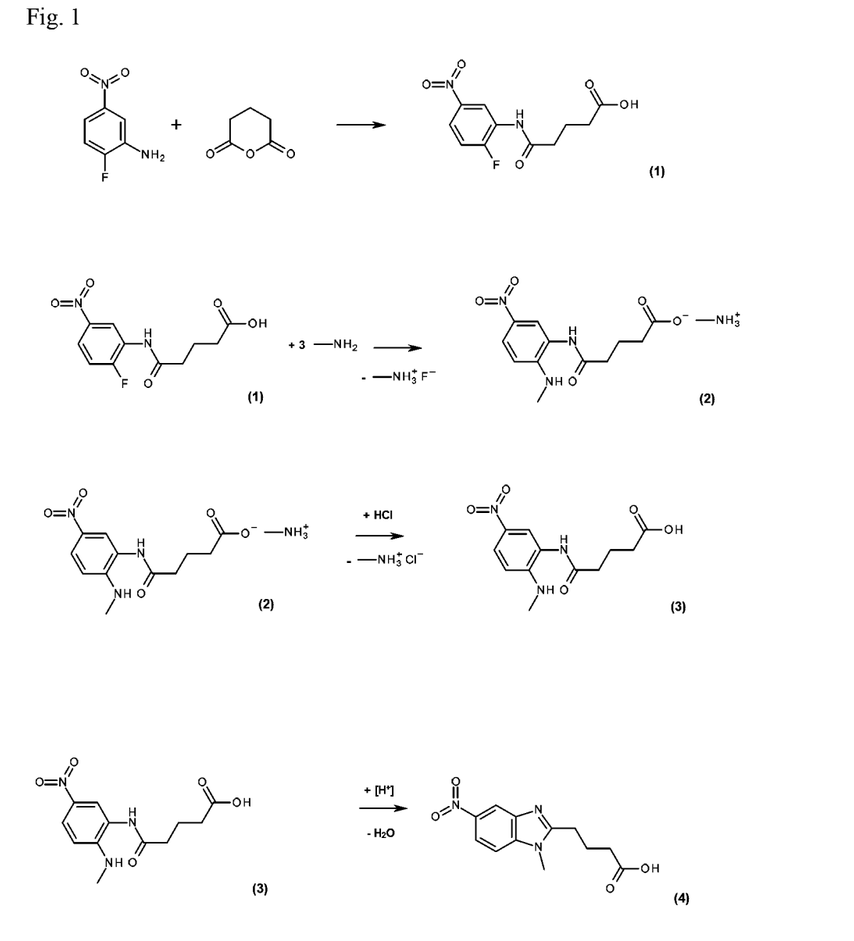
FIG. 1 shows the reaction sequence for the preparation of 4-(1-methyl-5-nitro-1H-benzimidazol-2-yl)butanoic acid (4), starting from 2-fluoro-5-nitroaniline via the intermediates 5-(2-fluoro-5-nitroanilino)-5-oxopentanoic acid (1), methylammonium 5-[2-(methylamino)-5-nitroanilino]-5-oxopentanoate (2) and 5-[2-(methylamino)-5-nitroanilino]-5-oxopentanoic acid (3).

According to one aspect of the invention, a method for the preparation of 4-(1-methyl-5-nitrobenzimidazol-2-yl)butanoic acid (4) starting from 2-fluoro-5-nitroaniline is provided. Therein, 2-fluoro-5-nitroaniline is converted to 5-(2-fluoro-5-nitroanilino)-5-oxopentanoic acid (1, CAS No 451459-95-3) using glutaric anhydride in a step a).

(1)

The reaction product of step a) is subsequently converted to methylammonium 5-[2-(methylamino)-5-nitroanilino]-5-oxopentanoate (2) using methylamine in a step b), which is in turn converted in a step c) to the corresponding acid, 5-[2-(methylamino)-5-nitroanilino]-5-oxopentanoic acid (3, CAS-Nr. 91644-13-2).

(2)

(3)

In a step d), the reaction product (3) of step c) is condensed to 4-(1-methyl-5-nitro-1H-benzimidazol-2-yl)butanoic acid (4, CAS-Nr. 31349-48-1).

(4)

In one embodiment, the reaction steps a) to d) are performed in a single process step without isolation of the reaction products. The reactions can be performed in a one-pot laboratory process.

The use of glutaric anhydride in step a) is advantageous in comparison to the use of alternative reagents such as acid chlorides, as the formation of viscous by-products is reduced.

In one embodiment, the reaction of step a) is performed in a solvent that is chemically inert towards glutaric anhydride. Examples for such solvents include, without being restricted to, aliphatic, aromatic, cycloaliphatic or chlorinated hydrocarbons, ethers or carboxylic acid esters. Preferably, tetrahydrofuran or toluene is used.

In one embodiment of this aspect of the invention, the reaction of step b) is performed in an aqueous or alcoholic solution of methylamine, wherein the concentration of the aqueous or alcoholic methylamine solution is 25-40%, preferably 30%.

In one embodiment, the product of step d), 4-(1-methyl-5-nitro-1H-benzimidazol-2-yl)butanoic acid (4), is isolated.

Figure 2:
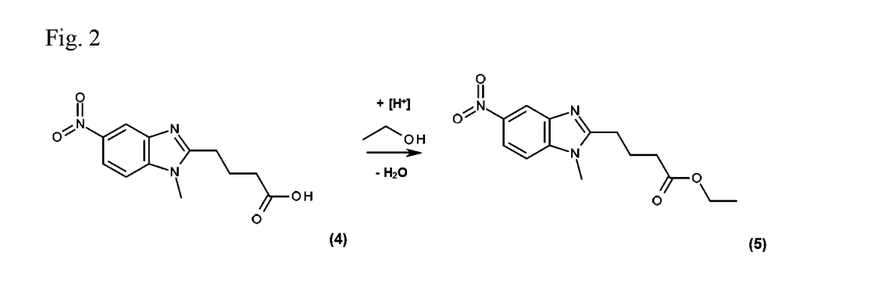
FIG. 2 shows the esterification of 4-(1-methyl-5-nitro-1H-benzimidazol-2-yl)butanoic acid (4) to ethyl 4-(1-methyl-5-nitro-1H-benzimidazol-2-yl)butanoate (5).

In one embodiment, the product of step d), 4-(1-methyl-5-nitro-1H-benzimidazol-2-yl)butanoic acid (4), is converted to alkyl 4-(1-methyl-5-nitro-1H-benzimidazol-2-yl)butanoate (5, CAS No 3543-72-4 (R=ethyl-)) in a step e), wherein R is $CH_3$ (methyl-), $C_2H_5$ (ethyl-), $C_3H_7$ (propyl-) or $C_4H_9$ (butyl-), generally $C_nH_{2n+1}$.

(5)

The reaction of step e) is performed with a primary or secondary C1 to C4 alcohol.

In one embodiment the reaction is performed with methanol, 1-propanol, 2-propanol, 1-butanol, 2-methyl-1-propanol or 2-butanol, preferably with ethanol.

In one embodiment, the reaction is performed in the presence of a strong acid. A strong acid in the sense of the present specification is defined by a $pK_A$ value <1.5. Preferably, sulfuric acid ($H_2SO_4$) is used.

In one embodiment, the amount of acid employed ranges from 10-90% in relation to the amount of substance of the product of step d), 4-(1-methyl-5-nitro-1H-benzimidazol-2-yl)butanoic acid (4) used, preferably 60-75%.

The process disclosed in DD 34727 uses more than 150% acid based on the molar quantity of the product of step d) used. The yields that are achieved under these reaction conditions are thereby lower than those achieved by the method presented herein (76% versus 88%). Thus, compared with the prior art, the yields are significantly increased by 12%.

In one embodiment, R is ethyl.

In a further embodiment of this aspect of the invention, the steps a) to e) are performed in a single process step without isolation of the reaction products.

Therein, the methylammonium 5-[(2-methylamino-5-nitrophenyl)amino]-5-oxopentanoate (2) is concentrated to dryness under vacuum. To remove residual water and further methylamine gas, the material is concentrated multiple times firstly from propanol and finally from ethanol to give a solid residue. Following addition of identical quantities of ethanol and acid as per an isolation according to step d), step e) is immediately instigated and the compound alkyl 4-(1-methyl-5-nitro-1H-benzimidazol-2-yl) butanoate (5, CAS No 3543-72-4 (R=ethyl-)) obtained in the same fashion. The advantage of this procedure is that a further step is added to the one-pot procedure.

Due to the formation of hydrogen fluoride during the reaction, the procedure must be carried out in an apparatus being inert toward hydrogen fluoride.

A further embodiment of the production of alkyl 4-(1-methyl-5-nitro-1H-benzimidazol-2-yl) butanoate (5, CAS No 3543-72-4 (R=ethyl-)) entails initially heating 2-fluoro-5-nitroaniline with aqueous or alcoholic methylamine solution at 80-90° C. over several hours yielding compound N-1-methyl-4-nitrobenzen-1,2-diamine (CAS 41939-61-1), whereby the concentration of the methylamine solution is 25-40%, preferably 30%.

The resulting compound N-1-methyl-4-nitrobenzene-1,2-diamine (CAS 41939-61-1) is subsequently converted to 5-[(2-methylamino-5-nitrophenyl)amino]-5-oxopentaneoic acid (3, CAS-Nr. 91644-13-2) using glutaric acid anhydride in tetrahydrofuran. Complete concentration to dryness leaves compound (3).

Compound (3) is then converted to 4-(1-methyl-5-nitro-1H-benzimidazol-2-yl)butanoic acid-alkyl ester (5, CAS-Nr. 3543-72-4 (R=Ethyl-)) using ethanol and acid catalyst in the same ratio as with the compound 4-(1-methyl-5-nitro-1H-benzimidazol-2-yl)butanoic acid (4, CAS-Nr. 31349-48-1) in step e).

In comparison to the earlier described process, a challenge of this procedure is that the conversion to N-1-Methyl-4-nitrobenzene-1,2-diamine (CAS 41939-61-1) requires higher excesses and proceeds significantly slower (here >10 hours compared to max. 2 hours). In addition, the compound to be isolated and dried is strongly electrostatically chargeable, which leads to substantial handling difficulties.

Figure 3:
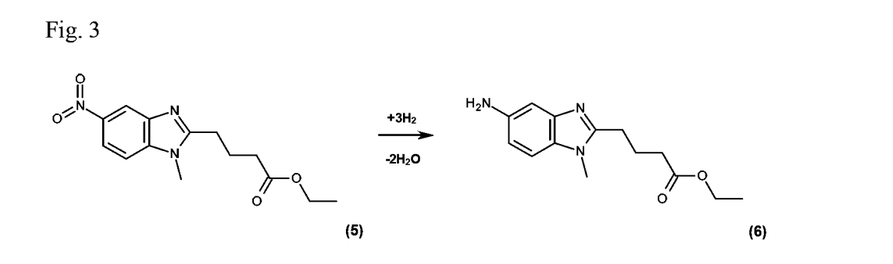
FIG. 3 shows the hydrogenation of ethyl 4-(1-methyl-5-nitro-1H-benzimidazol-2-yl)butanoate (5) to ethyl 4-(5-amino-1-methyl-1H-benzimidazol-2-yl)butanoate (6).

In one embodiment of the invention, a method for the preparation of alkyl 4-(5-amino-1-methyl-1H-benzimidazol-2-yl)butanoate (6, CAS No 3543-73-5 (R=ethyl-)) through selective reduction of compound (5) is provided, wherein R is $CH_3$ (methyl-), $C_2H$, (ethyl-), $C_3H_7$ (propyl-) or $C_4H_9$ (butyl-), generally $C_nH_{2n+1}$.

(6)

In one embodiment, the reduction is performed with hydrogen using a palladium catalyst doped with iron. The use of catalysts based on palladium doped with iron is advantageous in comparison to the use of catalysts based on platinum doped with vanadium, as the formation of intermediates or by-products is strongly suppressed and, consequently, the synthesis can be designed to be more economical. With the use of pure palladium catalysts increased levels of by-products occur towards the end of the hydrogenation which, through several recrystallizations with loss of yield, are only moderately removable.

In one embodiment, the palladium catalyst is doped with iron.

In one embodiment, an additional iron (II) or iron (III) salt of an organic or inorganic acid is added in catalytic amounts to the used catalyst.

In one embodiment, the additional iron (II) or iron (III) salt is selected from iron (II) sulfate-7-hydrate, iron (III) nitrate-9-hydrate, iron (III) acetylacetonate and iron (III)-sulfate-5-hydrate are suitable.

In one embodiment, the reaction for the preparation of compound (6) is performed in an organic solvent.

In one embodiment, the organic solvent is tetrahydrofuran, ethyl acetate, methanol or ethanol. Ethanol is preferred.

Figure 4:
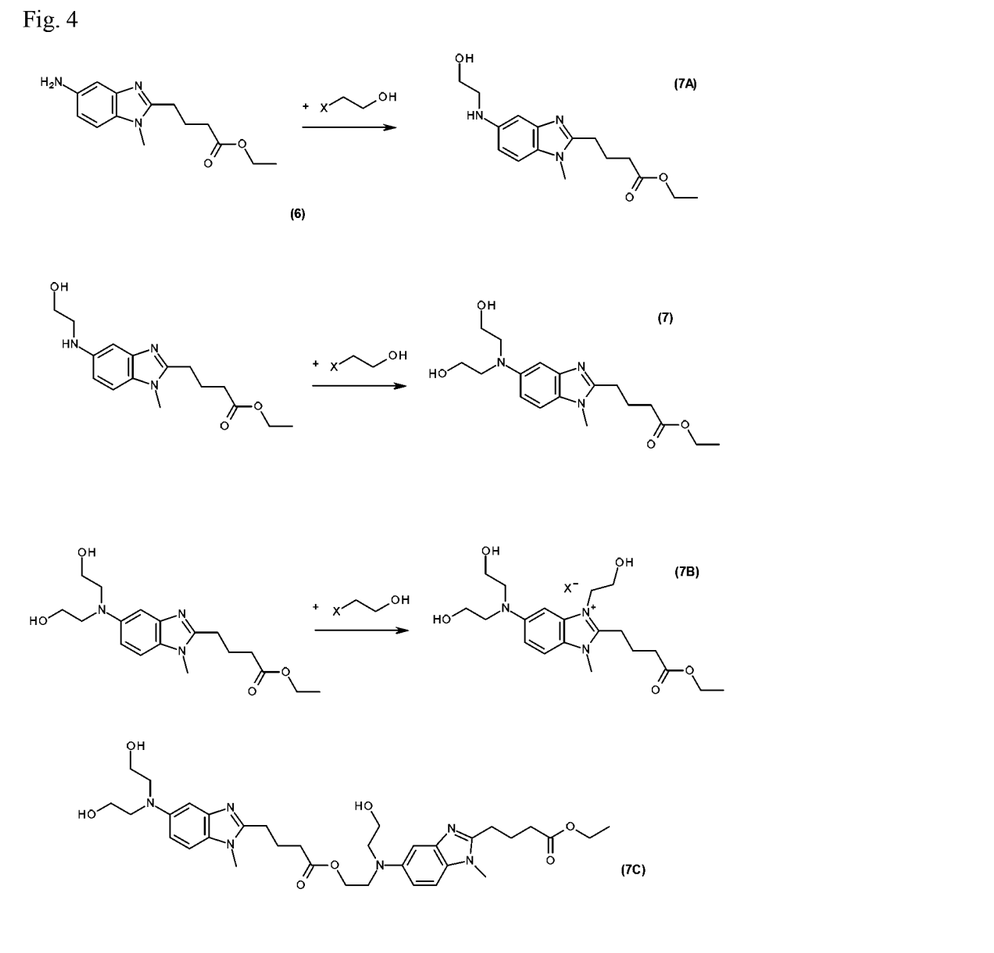
FIG. 4 shows the alkylation of ethyl 4-(5-amino-1-methyl-1H-benzimidazol-2-yl)butanoate (6) to ethyl 4-[5-[bis(2-hydroxyethyl)amino]-methyl-1H-benzimidazol-2-yl]butanoate (7) with the intermediate ethyl 4-[5-(2-hydroxyethylamino-1-methyl-1H-benzimidazole-2-yl]butanoate (7A) as well as the undesired over-alkylation product 6-[bis-(2-hydroxyethyl)-amino]-2-(3-ethoxycarbonyl-propyl)-1-(2-hydroxyethyl)-3-methyl-3H-benzimidazol-1-iumhalogenide (7B) and the undesired dimer (7C) of compound (7).

In one embodiment, the compound alkyl 4-(5-amino-1-methyl-1H-benzimidazol-2-yl)butanoate (6) is alkylated to alkyl 4-[5-[bis(2-hydroxyethyl)amino]-1-methyl-1H-benzimidazol-2-yl]butanoate (7, CAS No. 3543-74-6 (R=ethyl-)), wherein R is $CH_3$ (methyl), $C_2H_5$ (ethyl-), $C_3H_7$ (propyl-) or $C_4H_9$ (butyl-), generally $C_nH_{2n+1}$.

(7)

In one embodiment, the alkylation is performed with ethylene oxide or a 2-haloethanol.

In one embodiment, the 2-haloethanol is 2-chloroethanol. In one embodiment, the 2-haloethanol is 2-bromoethanol. In one embodiment, the 2-haloethanol is 2-iodoethanol.

In one embodiment, an alkali metal- or earth alkaline metal iodide, in particular sodium or potassium iodide, is added to accelerate the reaction. Thereby, the reaction time is shortened by approx. 30% through the use of 2-bromoethanol and potassium iodide.

In one embodiment, the reaction for the preparation of alkyl 4-[5-[bis(2-hydroxyethyl)amino]-1-methyl-1H-benzimidazol-2-yl]butanoate (7) is performed in water, a C1- to C4-alkyl alcohol or a mixture of water and alcohol.

In one embodiment, the alcohol is selected from methanol, ethanol, 1-propanol, 2-propanol, 1-butanol, 2-methyl-1-propanol, 2-butanol or 2-methyl propan-2-ol.

In one embodiment, the alkylation is performed at pH values <9.1, preferably at pH values between 4 and 8, in particular at pH values between 4.0 and 5.5.

In one embodiment, the alkylation is performed in water.

In one embodiment, the alkylation is performed at a temperature of 50° C. to 80° C., preferably at 60° C. to 70° C.

In one embodiment, the pH value is controlled by the addition of salt and/or buffer solutions of acetic acid/alkali metal acetate, ammonium- or alkali metal hydrogen carbonates, ammonium-, alkali metal or alkaline earth metal carbonate, ammonium-, mono-, di- or trimethyl-ammonium acetate, mono-, di- or triethylammonium acetate, ammonium propionate, disodium hydrogenphosphate, dipotassium hydrogenphosphate, diammonium hydrogenphosphate alone or in combination with commercial "ammonium carbonate" (1:1 mixture of ammonium hydrogen carbonate and ammonium carbonate), ammonium hydrogen carbonate or general salts of a weak to medium strength acid (citric acid, tartaric acid, succinic acid, malonic acid or oxalic acid) in the form of the ammonium-, alkylammonium-, alkali metal or alkali earth metal salts.

In one embodiment, the alkylation step is performed with 2-bromoethanol in water by the addition of ammonium acetate at the outset of the reaction at pH 4 to 6 without addition of other organic or inorganic bases.

In one embodiment, the pH value of this system for the alkylation during the main reaction lies between pH 4.2 to 5.5. Towards the end of the reaction the pH value can or may be lowered to 4 without instigating noticeable ester cleavage. Lower pH values and raised temperatures (> approx. 75° C.) effect clear ester cleavage and a sharp reduction of yield and quality.

By performing the method of the invention with addition of the stated salts individually or in combination, an otherwise unavoidable over-alkylation is markedly reduced. This over-alkylation arises quickly and in increasing quantities at pH values >6.5. This is also the case with all procedures described hitherto involving the use of organic or inorganic bases, as these are already added at the outset of the reaction. The yield dramatically drops as the proportion of over-alkylated product increases.

In one embodiment, the alkylation is performed with a molar ratio of >8 mol 2-haloethanol (2-chloroethanol, 2-bromoethanol or 2-iodoethanol) to 1 mol alkyl 4-(5-amino-1-methyl-1H-benzimidazol-2-yl)butanoate (6, CAS No 3543-73-5 (R=ethyl-)). It is advantageous thereby to utilise, for example, 10 mol 2-bromoethanol. Thereby, an otherwise significant side reaction which forms a dimeric compound such as compound 7C is strongly suppressed. In comparison to all other by-products, this dimeric compound cannot be removed through recrystallisation.

In one embodiment, the pH of the alkylation reaction is controlled through addition of salt and/or buffer solutions, wherein a molar ratio of >2 mol of salt- and/or buffer solution to 1 mol compound (6) is used.

In one embodiment, a molar ratio of 3 mol ammonium acetate to 1 mol compound (6) is used.

In one embodiment, the alkylation is performed with 2-bromoethanol with a molar ration of >8 mol bromoethanol to 1 mol alkyl 4-(5-amino-1-methyl-1H-benzimidazol-2-yl)

butanoate (6, CAS No 3543-73-5 (R=ethyl-), whereby particularly the formation of a dimer of compound (7) such as compound (7C) is suppressed particularly below a content of 0.15%, and with addition of an alkali metal- or earth alkaline metal iodide, in particular sodium or potassium iodide, whereby particularly the alkylation is accelerated, particularly to 70% of the reaction time without addition.

Figure 5:
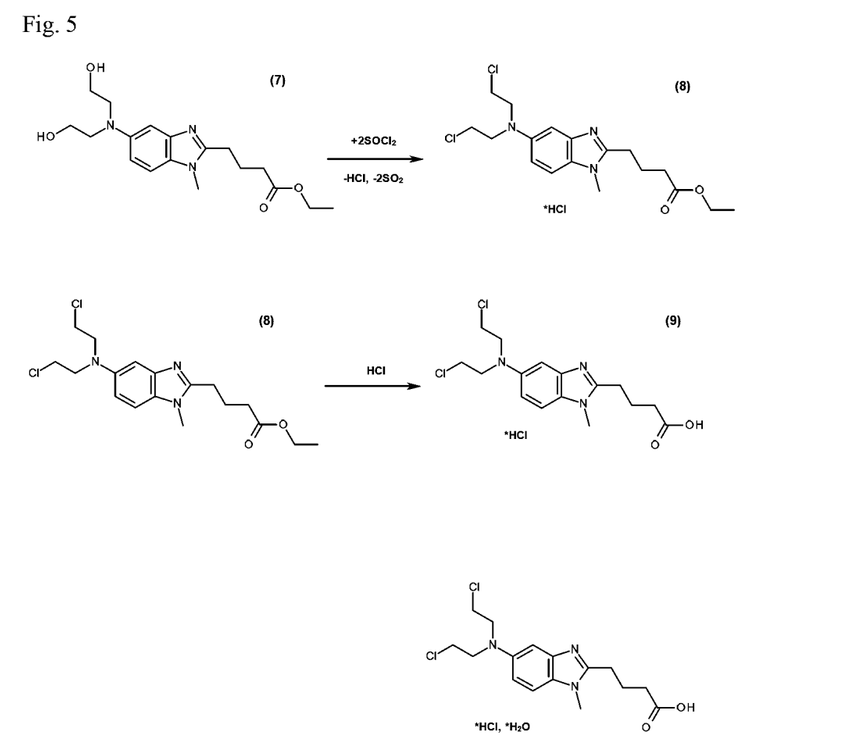
FIG. 5 shows the chlorination and subsequent hydrolysis of ethyl 4-[5-[bis(2-hydroxyethyl)amino]-1-methyl-1H-benzimidazol-2-yl]butanoate (7) to 4-[5-[bis(2-chloroethyl)amino]-1-methyl-1H-benzimidazol-2-yl]butanoic acid (9, Bendamustine) via the intermediate ethyl 4-[5-[bis(2-chloroethyl)amino]-1-methyl-1H-benzimidazol-2-yl]butanoate (8).

In one embodiment, compound (7) is chlorinated to alkyl 4-[5-[bis(2-chloroethyl)amino]-1-methyl-1H-benzimidazol-2-yl]butanoate (8, CAS No. 87475-54-5 (R=ethyl-)) with a suitable chlorinating agent, wherein R is CH$_3$ (methyl-), C$_2$H, (ethyl-), C$_3$H$_7$ (propyl-) or C$_4$H$_9$ (butyl-), generally C.

(8)

In one embodiment, the chlorinating agent is thionyl chloride (SOCl$_2$), sulfuryl chloride (SO$_2$Cl$_2$), phosphorus oxychloride (POCl$_3$), phosphorus trichloride (PCl$_3$) or phosphorus pentachloride (PCl$_5$). Thionyl chloride (SOCl$_2$) is a preferred chlorinating agent.

In one embodiment of this aspect of the invention, the reaction is performed in a chlorinated hydrocarbon solvent, in particular dichloromethane or trichloromethane.

In another embodiment, the reaction is carried out in aromatic solvents, in particular in toluene or chlorobenzene.

In one embodiment, product (8) exists as a water-soluble hydrochloride or analogous salt thereof.

In one embodiment, compound (8) is hydrolysed to 4-[5-[bis(2-chloroethyl)amino]-1-methyl-1H-benzimidazol-2-yl]butanoic acid (9, Bendamustine, CAS-Nr. 16506-27-7).

(9)

In one embodiment, the hydrolysis of compound (8) is performed with aqueous hydrochloric acid.

In one embodiment, product (9) is available as water-soluble hydrochloride (CAS-Nr. 3543-75-7) or as an analogous salt thereof.

Figures 6, 7:
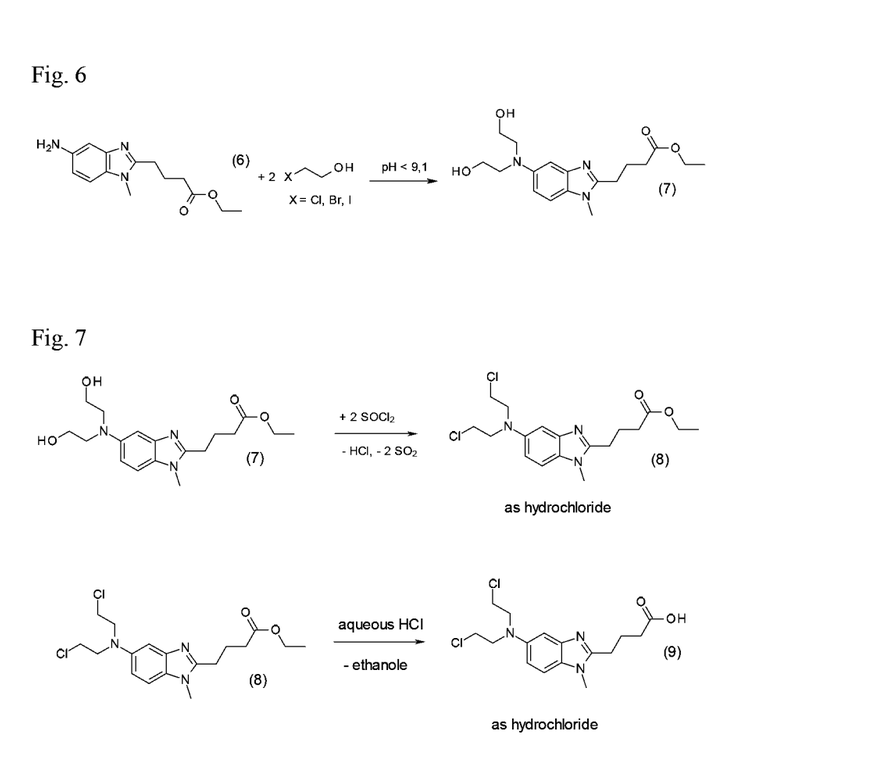
FIG. 6 shows the alkylation of ethyl 4-(5-amino-1-methyl-1H-benzimidazol-2-yl)butanoate (6) to ethyl 4-[5-[bis(2-hydroxyethyl)amino]-1-methyl-1H-benzimidazol-2-yl]butanoate (7).
FIG. 7 shows the chlorination and subsequent hydrolysis of ethyl 4-[5-[bis(2-hydroxyethyl)amino]-1-methyl-1H-benzimidazol-2-yl]butanoate (7) to 4-[5-[bis(2-chloroethyl)amino]-1-methyl-1H-benzimidazol-2-yl]butanoic acid (9, Bendamustine) via the intermediate ethyl 4-[5-[bis(2-chloroethyl)amino]-1-methyl-1H-benzimidazol-2-yl]butanoate (8).

According to another aspect of the invention, a method for the preparation of the intermediate 4-[5-[bis(2-hydroxyethyl)amino]-1-methyl-1H-benzimidazol-2-yl]butanoate (7, CAS No. 3543-74-6 (R=ethyl-)) starting from 4-(5-amino-1-methyl-1H-benzimidazol-2-yl)butanoate (6) is provided.

The compound 4-[5-[bis(2-hydroxyethyl)amino]-1-methyl-1H-benzimidazol-2-yl]butanoate (7) is prepared by a conversion of 4-(5-amino-1-methyl-1H-benzimidazol-2-yl)butanoate (6, CAS No 3543-73-5 (R=ethyl-)) with 2-haloethanol, wherein R is CH$_3$ (methyl-), C$_2$H$_5$ (ethyl), C$_3$H$_7$ (propyl-) or C$_4$H$_9$ (butyl-) and wherein the reaction is performed in an aqueous acetic acid/acetate buffer system or in the presence of an aqueous acetate solution, without the addition of further organic or inorganic bases.

(6)

(7)

In one embodiment, the compound 4-(5-amino-1-methyl-1H-benzimidazol-2-yl)butanoate (6, CAS No 3543-73-5 (R=ethyl-)) is alkylated with 2-haloethanol in an aqueous acetic acid/acetate buffer system with pH values of <9.1 to 4-[5-[bis(2-hydroxyethyl)amino]-1-methyl-1H-benzimidazol-2-yl]butanoate (7, CAS No. 3543-74-6 (R=ethyl-)), wherein R is CH$_3$ (methyl-), C$_2$H, (ethyl-), C$_3$H$_7$ (propyl-) or C$_4$H$_9$ (butyl-).

In one embodiment, the 2-haloethanol is 2-fluoroethanol, 2-chloroethanol, 2-bromoethanol or 2-iodoethanol. In one embodiment, the 2-haloethanol is 2-bromoethanol or 2-chloroethanol.

In one embodiment, the 2-haloethanol is 2-bromoethanol.

In one alternative embodiment, the reaction for the preparation of 4-[5-[bis(2-hydroxyethyl)amino]-1-methyl-1H-benzimidazol-2-yl]butanoate (7) is performed in a C1- to C4-alkyl alcohol, wherein in particular methanol, ethanol, 1-propanol, 2-propanol, 1-butanol, 2-methyl-1-propanol, 2-butanol or 2-methyl propan-2-ol is used.

In one embodiment, the alkylation is performed at pH values between 4 to 8, preferably at pH values between 4 to 6, in particular at pH values between 4.5 to 5.5, wherein the pH-value is adjusted by the addition of a buffer solution or hydrogen carbonates, in particular by the addition of an aqueous acetic acid/acetate buffer system.

In one embodiment, the alkylation is performed at pH values <9.1.

In one embodiment, the alkylation is performed at pH values between 4 to 8.

In one embodiment, the alkylation is performed at pH values between 4.5 to 5.5.

A product yield of up to 85% is achieved with the herein describe reaction conditions, which is a significant increase compared with the previously described methods.

In one embodiment, compound (7) is subsequently chlorinated to 4-[5-[bis(2-chloroethyl)amino]-1-methyl-1H-benzimidazol-2-yl]butanoate (8, CAS No. 87475-54-5 (R=ethyl-)) with a suitable chlorinating agent, wherein R is CH₃ (methyl-), C₂H₅ (ethyl-), C₃H₇ (propyl-) or C₄H₉ (butyl-).

(8)

In one embodiment, the chlorinating agent is thionyl chloride (SOCl₂), sulfuryl chloride (SO₂Cl₂), phosphorus oxychloride (POCl₃), phosphorus trichloride (PCl₃) or phosphorus pentachloride (PCl₅).

In one embodiment, thionyl chloride (SOCl₂) is used as the chlorinating agent.

In one embodiment, the reaction is performed in a chlorinated hydrocarbon solvent, in particular dichloromethane or trichloromethane.

In another embodiment, the reaction is carried out in aromatic solvents, in particular in toluene or chlorobenzene.

In one embodiment, the reaction is performed in dichloromethane.

In one embodiment, compound (8) is hydrolysed to 4-[5-[bis(2-chloroethyl)amino]-1-methyl-1H-benzimidazol-2-yl]butanoic acid (9, Bendamustine, CAS-Nr. 16506-27-7) or its hydrochloride.

(9)

In one embodiment, the hydrolysis of compound (8) is performed with aqueous hydrochloric acid.

In one embodiment, product (9) is available as water-soluble hydrochloride (CAS-Nr. 3543-75-7) or as an analogous salt thereof.

Wherever reference is made herein to an embodiment of the invention, and such an embodiment refers to one feature of the invention only, it is intended that such an embodiment may be combined with any other embodiment which refers to a different feature.

The invention is further illustrated, without limitations, by the following figures and examples, from which further features, advantages or embodiments can be derived. The examples do not limit but illustrate the invention.

EXAMPLES

Example 1

Synthesis of 4-(-methyl-5-nitro-1H-benzimidazol-2-yl)butanoic acid (4)

95 g (608.5 mmol) of 2-fluoro-5-nitroaniline were dissolved together with 83.1 g (691.9 mmol) of glutaric anhydride (95%) in 490 g of toluene. Subsequently, the mixture was heated at ca. 85° C. for 4 h and the resulting crystal mush concentrated to dryness at up to 70° C. under vacuum.

To this dried crystal mush were added 284 g of 40% methylamine aqueous solution and 94 g water. The residue dissolved quickly and the mixture began to boil after a short time (15-25 minutes). The solution was held at 75° C. (to limit consumption of methylamine) for approximately 3 h and then diluted with 966 g of water and 680 g of propan-2-ol. 156 g of 37% hydrochloric acid were added with stirring at 55-60° C. to neutralize the reaction mixture.

Compound (4) was subsequently precipitated through further addition of 37% hydrochloric acid. The precipitate was filtered, washed with water and dried.

The yield of compound (4) was 157 g (596.4. mmol) with a content of >99%. (98.0% of theory).

Instead of 40% methylamine aqueous solution, also a 25% methylamine alcoholic solution, for example a methylamine methanol or ethanol solution, can be used.

Example 2

Synthesis of ethyl 4-(4-(1-methyl-5-nitro-1H-benzimidazol-2-yl)butanoate (5)

157 g (596.4 mmol) of compound (4) were suspended in 1374 g of ethanol, 43.8 g of 96% sulfuric acid were added and the reaction mixture heated for approx. 10 h under reflux before concentrating to the crystallization concentration. The catalytic acid was preferably neutralized with triethylamine, the crystallization initiated by cooling and then the precipitate filtered. Compound (5) was washed with ethanol and subsequently dried.

The yield of compound (5) was 163 g (559.5 mmol) with a content of >99% (93.8% of theory).

Example 3

Synthesis of ethyl 4-(5-amino-1-methyl-1H-benzimidazol-2-ylbutanoate (6)

163 g (559.5 mmol) of compound (5) were dissolved in 1875 g ethanol. 14 g of palladium catalyst on activated carbon doped with iron (5% Pd, 1% Fe) and an additional 0.8 g of iron (II) sulfate 7-hydrate or 0.8 g of iron (III) nitrate 9-hydrate were added. Compound (5) was 10 then hydrogenated at a hydrogen pressure of up to 4 bar until complete conversion of the starting compound (5).

The catalyst was removed by filtration, and the ethanolic solution concentrated until a dry product remained. This residue was crystallized from propan-2-ol or ethyl acetate.

The yield of compound (6) was 128 g (489.8 mmol) with a content of >99% (87.5% of theory).

The overall yield of compound (6) was 80.4% of theory in relation to 2-fluoro-5-nitroaniline. In comparison, the synthesis according to DD34727 starting from N-1-methyl-4-nitrobenzene-1,2-diamine (CAS 41939-61-1) is characterized by a yield of 39.0%.

Example 4

Synthesis of ethyl 4-[5-[bis(2-hydroxyethyl)amino]-1-methyl-1H-benzimidazol-2-yl]butanoate (7)

To a solution of 81.3 g (650.6 mmol) 2-bromoethanol, 1 g potassium iodide and 100 g water was added 17.0 g (65 mmol) compound (6). The reaction mixture was heated to 65-70° C. and held at this temperature for 8 h to 12 h. The pH value of the solution was held between 4.2-5.5 during this period by dropwise addition of a solution of 20.0 g (151.4 mmol) diammonium hydrogen phosphate in 35 g water. The control of pH over the duration of the reaction was effected through use of a pH electrode. The conversion was followed by HPLC. The reaction was continued until the fraction of compound (7A) was ≤1.5%. Thereby ca. 8% of compound (7B) had formed and the proportion of compound (7) was ca. 87%. The reaction mixture was subsequently concentrated to dryness at ca. 55-60° C. under vacuum. To the residue was added 150 g water and, preferably with an alkali metal carbonate, the pH value adjusted to ca. 8.5. The desired product (7) was extracted with 200 g methylene chloride or 225 g chloroform, and the organic phase subsequently washed with 60-80 g water. The organic phase was then concentrated to dryness and the remaining oil or already crystalline residue dissolved in 200 g ethyl acetate or alternatively in 60 g acetonitrile. Compound (7) crystallised at ca. 5° C. and was filtered under suction, washed with 20 g cold ethyl acetate or alternatively with 15 g cold acetonitrile and dried at 60-70° C. The yield of compound (7) was 18.3 g (52.4 mmol) with a content of ≥98.2% (80.5% of theory). The crude product contained ≤0.6% compound (7A) and compound (7B) respectively as well as <0.15% of compound (7C).

The crude product obtained was recrystallized from ethyl acetate, or alternatively from acetonitrile, toluene, propan-2-ol, tetrahydrofuran, acetone, isopopyl acetate or water, prior to further conversion to compound (8). Thereby the yield of compound (7) was 17.2 g (94.0% recrystallization yield) with a content of >99.2%, wherein compound (7A) was removed below a content of 0.2% and compound (7B) below 0.3%. Through the course of the reaction, the content of compound (7C) was kept below 0.15%, as this compound can only poorly be removed by recrystallization from the above described solvents. The overall yield of this step was 76.5% of theory and was thus ca. 12.5% higher than that described in the procedure using ethylene oxide as according to DD34727 and ca. 31% higher in comparison to the favoured procedure of WO2011079193 involving addition of Hünig's base.

Example 5

Synthesis of ethyl 4-[5-[bis(2-hydroxyethyl)amino]-1-methyl-1H-benzimidazol-2-yl]butanoate (7)

Analogous to Example 4 but with use of 6.9 g (65 mmol) sodium carbonate dissolved in 25 g water to hold the pH value between 4.2-5.5. Identical results in terms of yield and quality.

Example 6

Synthesis of ethyl 4-[5-[bis(2-hydroxyethyl)amino]-1-methyl-1H-benzimidazol-2-yl]butanoate (7)

Analogous to Example 4 but with use of 9.0 g (65 mmol) potassium carbonate dissolved in 12 g water to hold the pH value between 4.2-5.5. Identical results in terms of yield and quality.

Example 7

Synthesis of ethyl 4-[5-[bis(2-hydroxyethyl)amino]-1-methyl-1H-benzimidazol-2-yl]butanoate (7)

Analogous to Example 4 but with use of 19 g (109.1 mmol) dipotassium hydrogen phosphate dissolved in 25 g water to hold the pH value between 4.2-5.5. Identical results in terms of yield and quality.

Example 8

Synthesis of ethyl 4-[5-[bis(2-hydroxyethyl)amino]-1-methyl-1H-benzimidazol-2-yl]butanoate (7)

This example is a scaled-up analogue of Example 6 with use of 340 g (1.3 mol) compound (6), 2000 ml water and 1625 g (13 mol) 2-bromoethanol. The reaction was performed without potassium iodide at 69-70° C. The pH value was held between 4.2-5.5 using a solution of 138 g sodium carbonate

13

(1.3 mol) in 500 g water. Until a content of compound (7A) of 51.5% was reached, the duration of the reaction was 13.5 h. The yield of compound (7) was 365 g crude and 343.5 g after recrystallisation from acetonitrile (75.6% of theory).

Example 9

Synthesis of 4-[5-[bis(2-chloroethyl)amino]-1-methyl-1H-benzimidazol-2-yl]butanoic acid (9, Bendamustine hydrochloride hydrate)

250 g (0.7154 mol) compound (7) was dissolved in 2000 ml methylene chloride and 212 g (1.78 mol) thionyl chloride added at −1° C. within a period of 30 minutes. Thereby the temperature rose briefly to ca. 4° C. Following addition the reaction solution was stirred for a further 30 minutes at −1° C. The solution was then stirred for ca. 16 h at ca. 22° C. Thereafter the solvent and excess thionyl chloride were removed by distillation under vacuum. To hydrolyse the ester the remaining residue (compound 8 as its hydrochloride) was treated with 2.6 kg 37% hydrochloric acid and 1.4 l water, heated to ca. 75° C. and held at this temperature for 30-40 minutes. 25 g activated carbon was then added and stirred for 10 minutes at 75° C. The solution was filtered and concentrated under vacuum. To crystallise crude compound (9) the residue was dissolved in 1000 ml water at ca. 55° C., the solution cooled to ca. −2° C. and then held at this temperature for ca. 30 minutes. The crude product (9) was filtered off, washed with 250 g water and 200 g acetone and dried for 2 h at ca. 35° C. under vacuum.

The yield of crude compound (9) was 245 g (0.5936 mol) and had a water content of 4.5% (83% of theory).

245 g compound (9) were dissolved in 330 g 37% hydrochloric acid at ca. 40° C., treated with 1.28 kg water (temperature ca. 35° C.) and 650 g acetone (temperature ca. 35° C.) and stirred for 10 minutes. Crystallisation was initiated by the addition of 0.5 g Bendamustine hydrochloride hydrate, the mixture cooled within a period of 2 h to ca. −20° C. and then held at this temperature for ca. 90 minutes.

The precipitate was filtered under suction. The crystals were washed initially with a mixture of 120 g water and 90 g acetone and subsequently with 275 g acetone.

The pure Bendamustine hydrochloride hydrate was dried for ca. 2 h at ca. 35° C. under vacuum. Thus 225 g (0.545 mol) of pure (>99.8% content) compound (9) was obtained with an overall yield of 76.2% for this step.

Through drying of the Bendamustine hydrochloride hydrate under vacuum at ca. 50° C. the water content could be adjusted to ca. 1% in contrast to 4.4% of the mono hydrates.

Example 10

Synthesis of ethyl 4-[5-[bis(2-hydroxyethyl)amino]-1-methyl-1H-benzimidazol-2-yl]butanoate (7)

To a solution of (6) (5.00 g, 19 mmol) in a mixture of acetic acid (6.84 g, 114 mmol)/natrium acetate (9.35 g, 114 mmol) and water (100 g) bromoethanol (9.50 g, 76 mmol) is added. The reaction mixture is heated to 60-70° C. and held at this temperature for approximately 12 h. The conversion is followed by thin-layer chromatography. The mixture is cooled down, the pH value is set with NaOH to 8-9 and the reaction mixture is extracted with dichloromethane (approx. 100 ml), when a complete conversion of the starting substance is reached. The extract is washed with water (50 ml) and reduced under vacuum. Ethyl acetate (75 ml) is added to the residual oil. The mixture is warmed until a clear solution is reached and slowly cooled to 0° C., wherein the product crystallises. The product was filtered, washed with a small amount of ethyl acetate and dried under vacuum. The yield of compound (7) amounts to 5.48 g (82% of theory).

The crude product obtained was, before a further reaction, recrystallised from ethyl acetate. Thereby the yield of compound (7) was 4.93 g (90.0% of theory).

Example 11

Synthesis of ethyl 4-[5-[bis(2-hydroxyethyl)amino]-1-methyl-1H-benzimidazol-2-yl]butanoate (7)

To a solution of compound (6) (5.00 g, 19 mmol) in water (100 g) bromoethanol (9.50 g, 76 mmol) is added. The reaction mixture is heated to 60-70° C. and held at this temperature for approximately 12 h. The pH value of the reaction is monitored and held in the range of 4-6 by a successive addition of an aqueous natrium acetate solution. The conversion is followed by thin-layer chromatography. The mixture is cooled down, the pH value is set with NaOH to 8-9 and the reaction mixture is extracted with dichloromethane (approx. 100 ml), when a complete conversion of the starting substance is reached. The extract is washed with water (50 ml) and reduced under vacuum. Ethyl acetate (75 ml) is added to the residual oil. The mixture is warmed until a clear solution is reached and slowly cooled to 0° C., wherein the product crystallises. The product was filtered, washed with a small amount of ethyl acetate and dried under vacuum. The yield of compound (7) amounts to 5.68 g (85% of theory).

The crude product obtained was, before a further reaction, recrystallised from ethyl acetate. Thereby the yield of compound (7) was 5.00 g (88.0% of theory).

Example 12

Synthesis of 4-[5-[bis(2-chloroethyl)amino]-1-methyl-1H-benzimidazol-2-yl]butanoic acid (9, Bendamustine)

To a solution of compound (7) (5.00 g, 14 mmol) in 40 ml methylene chloride thionyl chloride (4.26 g, 36 mmol) is added at 5° C. Afterwards, the solution is stirred at ambient temperature for 16 h. The solvent is removed by distillation under vacuum. To the thereby produced brown oil 45 ml of 37% hydrochloric acid and 30 ml water is added and heated to 95° C. for 30 min. Subsequently 0.9 g activated carbon is added and stirred for 10 minutes at 95° C. The product is filtered and concentrated under vacuum until a dried product is formed. Afterwards a crystallisation of compound (9) is carried out in 20 ml water. The product was filtered, washed with water and acetone and dried under vacuum for 2 h at 50° C. The yield of compound (9) amounts to 4.3 g (11 mmol) with a content >99% (73% of theory).

We claim:

1. A method for the preparation of 4-(1-methyl-5-nitro-1H-benzimidazol-2-yl)butanoic acid (4), from 2-fluoro-5-nitroaniline, comprising the steps:

a) conversion of 2-fluoro-5-nitroaniline to 5-(2-fluoro-5-nitroanilino)-5-oxopentanoic acid (1) using glutaric anhydride:

(1)

b) conversion of the reaction product (1) of step a) to methyl ammonium 5-[2-(methylamino)-5-nitroanilino]-5-oxopentanoic (2) using methylamine:

(2)

c) conversion of the reaction product (2) of step b) to 5-[2-(methylamino)-5-nitroanilino]-5-oxopentanoic acid (3):

(3)

and
d) condensation of the reaction product (3) of step c) to 4-(1-methyl-5-nitro-1H-benzimidazol-2-yl)butanoic acid (4):

(4)

2. The method according to claim 1, wherein steps a) to d) are performed in a single process step without isolation of the reaction products.

3. The method according to claim 1, wherein tetrahydrofuran is used as a solvent.

4. The method according to claim 1, wherein the product of step d), 4-(1-methyl-5-nitro-1H-benzimidazol-2-yl)butanoic acid (4), is converted in a step e) with a C1- to C4-alkyl alcohol to alkyl 4-(1-methyl-5-nitro-1H-benzimidazol-2-yl) butanoate (5) in the presence of a strong acid, wherein R is methyl, ethyl, propyl, or butyl:

(5)

5. The method according to claim 4, wherein the amount of said strong acid in step e) is from 10-90% in relation to the amount of substance of the product 4-(1-methyl-5-nitro-1H-benzimidazol-2-yl)butanoic acid (4) of step d).

6. The method according to claim 4, wherein steps a) to e) are performed in a single process step without isolation of the reaction products.

7. The method according to claim 4, wherein the reaction product alkyl 4-(1-methyl-5-nitro-1H-benzimidazol-2-yl) butanoate (5) is converted to alkyl 4-(5-amino-1-methyl-1H-benzimidazol-2-yl)butanoate (6) through selective reduction of the nitro group, wherein R is methyl, ethyl, propyl, or butyl:

(6)

8. The method according to claim 7, wherein said reduction is performed with hydrogen using an iron-doped palladium catalyst.

9. The method according to claim 8, wherein an iron (II) or iron (III) salt of an organic or inorganic acid is added to said iron-doped palladium catalyst.

10. The method according to claim 7, wherein the reaction product alkyl 4-(5-amino-1-methyl-1H-benzimidazol-2-yl) butanoate (6) is alkylated to alkyl 4-[5-[bis(2-hydroxyethyl) amino]-1-methyl-1H-benzimidazol-2-yl]butanoate (7), wherein R is methyl, ethyl, propyl, or butyl:

(7)

11. The method according to claim 10, wherein the alkylation is performed with ethylene oxide or a 2-haloethanol.

12. The method according to claim 11, wherein the reaction is performed in an aqueous acetic acid/acetate buffer system at pH 4 to 6.

13. The method according to claim 10, wherein the reaction product alkyl 4-[5-[bis(2-hydroxyethyl)amino]-1-methyl-1H-benzimidazol-2-yl]butanoate (7) is converted to alkyl 4-[5-[bis(2-chloromethyl)amino]-1-methyl-1H-benzimidazol-2-yl]butanoate (8) with a chlorinating agent, wherein R is methyl, ethyl, propyl, or butyl:

14. The method according to claim 13, wherein said chlorinating agent is thionyl chloride.

15. The method according to claim 13, wherein alkyl 4-[5-[bis(2-chloroethyl)amino]-1-methyl-1H-benzimidazol-2-yl]butanoate (8) is hydrolysed to 4-[5-[bis(2-chloro-ethyl)-amino]-1-methyl-1H-benzimidazol-2-yl]butanoic acid (9, Bendamustine) or the hydrochloride thereof:

* * * * *